United States Patent
Proksa et al.

(10) Patent No.: US 10,806,422 B2
(45) Date of Patent: Oct. 20, 2020

(54) APPARATUS FOR GENERATING X-RAYS

(71) Applicant: KONINKLIJKE PHILIPS N.V., Eindhoven (NL)

(72) Inventors: Roland Proksa, Neu Wulmstorf (DE); Daniela Muenzel, Munich (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/097,636

(22) PCT Filed: May 24, 2017

(86) PCT No.: PCT/EP2017/062531
§ 371 (c)(1),
(2) Date: Oct. 30, 2018

(87) PCT Pub. No.: WO2017/207383
PCT Pub. Date: Dec. 7, 2017

(65) Prior Publication Data
US 2019/0133541 A1 May 9, 2019

(30) Foreign Application Priority Data
May 31, 2016 (EP) .................................... 16172185

(51) Int. Cl.
*A61B 6/00* (2006.01)
*H05G 1/20* (2006.01)
(Continued)

(52) U.S. Cl.
CPC .......... *A61B 6/5258* (2013.01); *H01J 35/045* (2013.01); *H01J 35/06* (2013.01);
(Continued)

(58) Field of Classification Search
CPC ...... A61B 6/5258; H01J 35/045; H01J 35/06; H01J 35/08; H05G 1/085; H05G 1/20; H05G 1/58
See application file for complete search history.

(56) References Cited

U.S. PATENT DOCUMENTS

| 4,551,800 A | 11/1985 | Riederer |
| 9,247,919 B2 | 2/2016 | Goshen |

(Continued)

FOREIGN PATENT DOCUMENTS

WO 2011/161558 12/2011

OTHER PUBLICATIONS

Kak, et al., "Principles of Computerized Tomographic Imaging", Chapter 5 Aliasing Artifacts and Noise in CT Images, p. 177, 1999.
(Continued)

*Primary Examiner* — Courtney D Thomas
(74) *Attorney, Agent, or Firm* — Larry Liberchuk

(57) ABSTRACT

The present invention relates to an apparatus for generating X-rays. It is described to produce (210) with a power supply (30) a voltage. A cathode (22) of an X-ray source (20) is positioned (220) relative to an anode (24) of the X-ray source. Electrons are emitted (230) from the cathode. Electrons emitted from the cathode interact (240) with the anode with energies corresponding to the voltage. X-rays are generated (250) from the anode, wherein the electrons interact with the anode to generate the X-rays. The X-ray source is controlled (260), such that a plurality of first X-ray pulses is generated each having a first X-ray flux, wherein the first X-ray pulses are temporally separated from each other. The X-ray source is controlled (270), such that a least one second X-ray pulse is generated having a second X-ray flux that is substantially less than the first X-ray flux, wherein the at least one second X-ray pulse is generated
(Continued)

temporally between consecutive pulses of the first X-ray pulses.

14 Claims, 8 Drawing Sheets

(51) Int. Cl.
*H05G 1/08* (2006.01)
*H01J 35/04* (2006.01)
*H01J 35/06* (2006.01)
*H01J 35/08* (2006.01)
*H05G 1/58* (2006.01)

(52) U.S. Cl.
CPC ............. *H01J 35/08* (2013.01); *H05G 1/085* (2013.01); *H05G 1/20* (2013.01); *H05G 1/58* (2013.01)

(56) References Cited

U.S. PATENT DOCUMENTS

| | | |
|---|---|---|
| 2007/0147574 A1 | 6/2007 | Bernard |
| 2008/0240355 A1 | 10/2008 | Ohishi |
| 2013/0251097 A1 | 9/2013 | Zou |

OTHER PUBLICATIONS

Bertram, et al., "Directional Interpolation of Sparsely Sampled Cone-Beam CT Sinogram Data", IEEE International Symposium on Biomedical Imaging: Nano to Macro; 2004.

APPARATUS FOR GENERATING X-RAYS

CROSS REFERENCE TO RELATED APPLICATIONS

This application is the U.S. National Phase application under 35 U.S.C. § 371 of International Application No. PCT/EP2017/062531, filed May 24, 2017, published as WO 2017/207383 on Dec. 7, 2017, which claims the benefit of European Patent Application Number 16172185.7 filed May 31, 2016. These applications are hereby incorporated by reference herein.

FIELD OF THE INVENTION

The present invention relates to an apparatus for generating X-rays, to a system for imaging an object, to a method for generating X-rays, to a method for imaging an object, as well as to a computer program element and a computer readable medium.

BACKGROUND OF THE INVENTION

The general background of this invention is the field of X-ray tube technology and in particular X-ray tube technology for computed X-ray tomography. In Dual Layer detection (DL) used to obtain spectral image data, such spectral imaging suffers from an effect called noise induced bias. To obtain spectral information (such as VNC or Iodine maps) from DL detection the data from the two detector channels have to undergo a (non-linear) material separation process. The process tends to generate a bias for noisy input data. The bias has a significant negative impact on the quality of the images and becomes a problem for quantification.

SUMMARY OF THE INVENTION

It would be advantageous to have improved apparatus for generating X-rays, and an improved system for imaging an object using such an apparatus.

The object of the present invention is solved with the subject matter of the independent claims, wherein further embodiments are incorporated in the dependent claims. It should be noted that the following described aspects and examples of the invention apply also for the apparatus for generating X-rays, the system for imaging an object, the method for generating X-rays, the method for imaging an object and for the computer program element and the computer readable medium.

According to a first aspect, there is provided an apparatus for generating X-rays, comprising:

an X-ray source;
a power supply; and
a processing unit.

The power supply is configured to produce a voltage. The X-ray source comprises a cathode and an anode, wherein the cathode is positioned relative to the anode. The cathode and anode are operable such that electrons emitted from the cathode interact with the anode with energies corresponding to the voltage, and wherein the electrons interact with the anode to generate X-rays. The processing unit is configured to control the X-ray source, such that a plurality of first X-ray pulses is generated each having a first X-ray flux, wherein the first X-ray pulses are temporally separated from each other. The processing unit is also configured to control the X-ray source, such that at least one second X-ray pulse is generated having a second X-ray flux that is substantially less than the first X-ray flux. An energy spectrum of the X-rays in the plurality of first X-ray pulses is substantially the same as an energy spectrum of the X-rays in the at least one second X-ray pulse. The processing unit is configured such that the at least one second X-ray pulse is generated temporally between two consecutive pulses of the first X-ray pulses.

In this way, the apparatus is producing two types of pulse, a first high flux pulse and one or more second lower flux pulses between consecutive longer pulses, where a pulse with the higher flux has more total energy and hence a larger number of X-rays (i.e., X-ray photons) than a lower flux pulse. In this way, the higher flux pulses with high energy can be used to provide spectral energy data of an object, for example with a dual layer detector with one part of the detector detecting X-rays at a low energy and another part of the detector detecting X-rays at a high energy. At best, for such a dual layer detector each part of the detector will detect half of the total number of X-rays reaching the detector, whilst in practice one detector will have a higher signal count per pixel than the other. Such detectors suffer from electronic noise, and signal to noise due to shot noise scales as the square root of detected counts. Noisy input data, in addition to the intrinsic problems of such noisy signal leading to noisy spectral data, also causes specific problems in spectral data analysis, such as noise induced bias. Therefore, by sparse angular sampling where the detector is moving angularly around an object, by increasing the flux for particular pulses only those pulses can be used for spectral processing because there is increased signal to noise associated with those pulses. However, at the same time the high flux pulses and the low flux pulses can be used in the conventional way, with the detector summing together the low and high energy X-ray generated counts per pixel to obtain a spectrally integrated signal, in order to obtain a high resolution image of the object from all the available pulses. Because signals are now not spectrally resolved (e.g., the signals from the halves of the detector are combined), there is an increased overall signal per pixel and hence increased signal to noise, and this can be used to provide high resolution non-spectral image data. Furthermore, the spectral data are acquired for the object at the same orientation as the high flux pulses forming the non-spectral data (in other words there is absolute image registration for particular images) and spectral data acquired can be used to improve or augment the non-spectral data and the non-spectral data can be used to improve or augment the spectral data.

To put this another way, the apparatus provides for Hybrid sparse sampling for spectral purposes with full sampling for non-spectral purposes.

In an example, the processing unit is configured to control a pulse duration of the plurality of first X-ray pulses and configured to control a pulse duration of the at least one second X-ray pulse.

In other words, a pulse duration of each of the first X-ray pulses is controlled in order to provide the high X-ray flux, where each pulse can have the same pulse duration, and a pulse duration of the or each of the second X-ray pulses is controlled to provide the low X-ray flux, where each pulse can have the same pulse duration.

This provides an effective way of providing pulses having different fluxes, because it can be difficult to change currents rapidly.

In an example, an energy spectrum of the X-rays in the plurality of first X-ray pulses is substantially the same as an energy spectrum of the X-rays in the at least one second X-ray pulse. The ratio of the first X-ray flux to the second X-ray flux is substantially equal to the ratio of the pulse duration of each pulse of the plurality of first X-ray pulses to the pulse duration of the at least one second X-ray pulse.

In other words, the flux per unit time for each pulse is the same. In this way, the X-ray flux is controlled through control of the respective pulse durations of the first and second pulses, with the first pulses having a substantially longer duration that the second pulses.

In this way, the apparatus is producing two types of pulse, a first long pulse and one or more second shorter pulses of shorter duration between consecutive longer pulses, where a pulse with the longer duration has more total energy and hence a larger number of X-rays than a shorter pulse. In this way, the longer pulses with high energy can be used to provide spectral energy data of an object, for example with a dual layer detector with one part of the detector detecting X-rays at a low energy and another part of the detector detecting X-rays at a high energy. However, at the same time the longer pulses and the shorter pulses can be used in the conventional way, with the detector summing together the low and high energy X-rays per pixel to obtain a spectrally integrated signal, in order to obtain a high resolution image of the object from all the available pulses.

This provides for a simple system, where the X-ray source is driven in the same manner for both the high and low flux pulses, but the differing fluxes are governed by the pulse durations, thereby providing a simple and effective means to vary the fluxes as required.

In an example, the X-ray source comprises a switch configured to inhibit the interaction of electrons between the cathode and the anode. The processing unit is configured to control the X-ray source by controlling the switch.

In other words, a switch that could be coupled to the power supply or coupled to another means, is controlled by the processing unit to periodically allow electrons emitted from the cathode to interact with the anode to produce pulses of different durations.

In an example, the switch has a rise time of approximately 1 μs.

In this way a number of low flux pulses can be generated between the high flux pulses, enabling very high angular resolutions to be generated as the apparatus is used to rotate about an object due to short exposure times being achievable, and for a minimization in total scan time.

According to a second aspect, there is provided a system for imaging an object, comprising:
  an X-ray source;
  a power supply; and
  a processing unit.

The power supply is configured to produce a voltage. The X-ray source comprises a cathode and an anode, wherein the cathode is positioned relative to the anode. The cathode and anode are operable such that electrons emitted from the cathode interact with the anode with energies corresponding to the voltage, and wherein the electrons interact with the anode to generate X-rays. The processing unit is configured to control the X-ray source, such that a plurality of first X-ray pulses is generated each having a first X-ray flux, wherein the first X-ray pulses are temporally separated from each other. The processing unit is also configured to control the X-ray source, such that at least one second X-ray pulse is generated having a second X-ray flux that is substantially less than the first X-ray flux. The processing unit is configured such that the at least one second X-ray pulse is generated temporally between two consecutive pulses of the first X-ray pulses. The system further comprises:
  an X-ray detector.

The X-ray source is configured to be positioned relative to the X-ray detector such that at least a part of the region between them is an examination region for accommodating an object. The X-ray detector is configured to acquire first when a first one of the plurality of first X-ray pulses is generated, wherein the first data comprises spectral data. The X-ray detector is also configured to acquire second data when the at least one second X-ray pulse is generated. The X-ray detector is configured to acquire third data when a second one of the plurality of first X-ray pulses is generated, wherein the third data comprises spectral data. The processing unit is configured to generate spectrally resolved image data comprising the first data and the third data. The processing unit is also configured to generate spectrally integrated image data comprising the first data, the second data and the third data.

In this way, the hybrid system can use pulses of high flux, with a high number of X-rays (i.e., X-ray photons), to obtain spectral data, with these pulses having the potential for high signal to noise at the detector and having the potential to mitigate noise induced issues due to spectral processing, but use all the pulses to obtain conventional non-spectral data. In generating the non-spectral data, the spectral data obtained for the high flux pulses is converted to non-spectral data, for example by adding together the photons at different energies for each pixel, increasing the signal count and hence signal to noise but losing the spectral contrast information for that pixel.

To put this another way, the system enables a hybrid sparse sampling approach to combine the high image quality of moderate sparse or even full angular sampling for conventional imaging with the advantages of sparse sampling for spectral images.

In other words, the system enables that in a series of acquisition cycles with a relative low effective dose, one cycle is done with much higher dose. The reconstruction of the conventional and spectral data is then done differently. While the conventional image reconstruction uses all projections, and hence will not, or only moderately, suffer from angular sub-sampling, the spectral reconstruction uses only the sparse high flux views.

The non-spectral data can also be used to improve the spectral data, and the spectral data can also be used to improve the non-spectral data.

In an example, the processing unit is configured to determine at least one measure of noise in the second data and wherein the second data comprises spectral data. On the basis of the at least one measure of noise the processing unit is configured to generate spectrally resolved image data from the first data, the second data and the third data.

In other words, when the number of detected photons associated with the low flux pulse is high enough, this data can be used for generating the spectral image data as well as that from the high flux pulses, because inclusion will not detrimentally change the overall noise to a great extent. This enables data on the fly to be used to provide for spectral imaging, when that data is found to be suitable for such purposes, but not to be used when the data is too noisy.

In an example, the X-ray detector is configured to acquire energy dependent data at a first X-ray energy and acquire energy dependent data at a second X-ray energy.

In other words, the X-ray detector is spectrally sensitive (e.g., a dual layer detector). This provides for a simple means for acquiring spectral energy data useable to provide spectral imaging, but which can also be used for non-spectral imaging.

In an example, the first data comprises first energy dependent data at the first X-ray energy and first energy dependent data at the second X-ray energy, and the third data comprises third energy dependent data at the first X-ray energy and third energy dependent data at the second X-ray energy.

In an example, the second data comprises spectral data and the second data comprises second energy dependent data at the first X-ray energy and second energy dependent data at the second X-ray energy. The processing unit is configured to generate a first combined data from the first energy dependent data at the first X-ray energy and the first energy dependent data at the second X-ray energy, and generate a second combined data from the second energy dependent data at the first X-ray energy and the second energy dependent data at the second X-ray energy, and generate a third combined data from the third energy dependent data at the first X-ray energy and the third energy dependent data at the second X-ray energy. The spectrally integrated image data is generated from the first combined image, the second combined image and the third combined image.

According to a third aspect, there is provided a method for generating X-rays, comprising:
a) producing with a power supply a voltage;
b) positioning a cathode of an X-ray source relative to an anode of the X-ray source;
c) emitting electrons from the cathode;
d) interacting electrons emitted from the cathode with the anode with energies corresponding to the voltage;
e) generating X-rays from the anode, wherein the electrons interact with the anode to generate the X-rays;
f) controlling the X-ray source, such that a plurality of first X-ray pulses is generated each having a first X-ray flux, wherein the first X-ray pulses are temporally separated from each other;
g) controlling the X-ray source, such that a least one second X-ray pulse is generated having a second X-ray flux that is substantially less than the first X-ray flux, wherein the at least one second X-ray pulse is generated temporally between consecutive pulses of the first X-ray pulses. An energy spectrum of the X-rays in the plurality of first X-ray pulses is substantially the same as an energy spectrum of the X-rays in the at least one second X-ray pulse.

In a fourth aspect, there is provided a method for imaging an object, comprising:
a) generating X-rays from an X-ray source by:
producing with a power supply a voltage;
positioning a cathode of an X-ray source relative to an anode of the X-ray source;
emitting electrons from the cathode;
interacting electrons emitted from the cathode with the anode with energies corresponding to the voltage;
generating X-rays from the anode, wherein the electrons interact with the anode to generate the X-rays;
controlling the X-ray source, such that a plurality of first X-ray pulses is generated each having a first X-ray flux, wherein the first X-ray pulses are temporally separated from each other;
controlling the X-ray source, such that a least one second X-ray pulse is generated having a second X-ray flux that is substantially less than the first X-ray flux, wherein the at least one second X-ray pulse is generated temporally between consecutive pulses of the first X-ray pulses; the method further comprising:
b) positioning the X-ray source relative to an X-ray detector such that at least a part of the region between them is an examination region for accommodating an object;
c) acquiring first data when a first one of the plurality of first X-ray pulses is generated, wherein the first data comprises spectral data;
d) acquiring second data when the at least one second X-ray pulse is generated;
e) acquiring third data when a second one of the plurality of first X-ray pulses is generated, wherein the third data comprises spectral data;
f) generating spectrally resolved image data from the first data and the third data; and
g) generating spectrally integrated image data from the first data, the second data and the third data.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
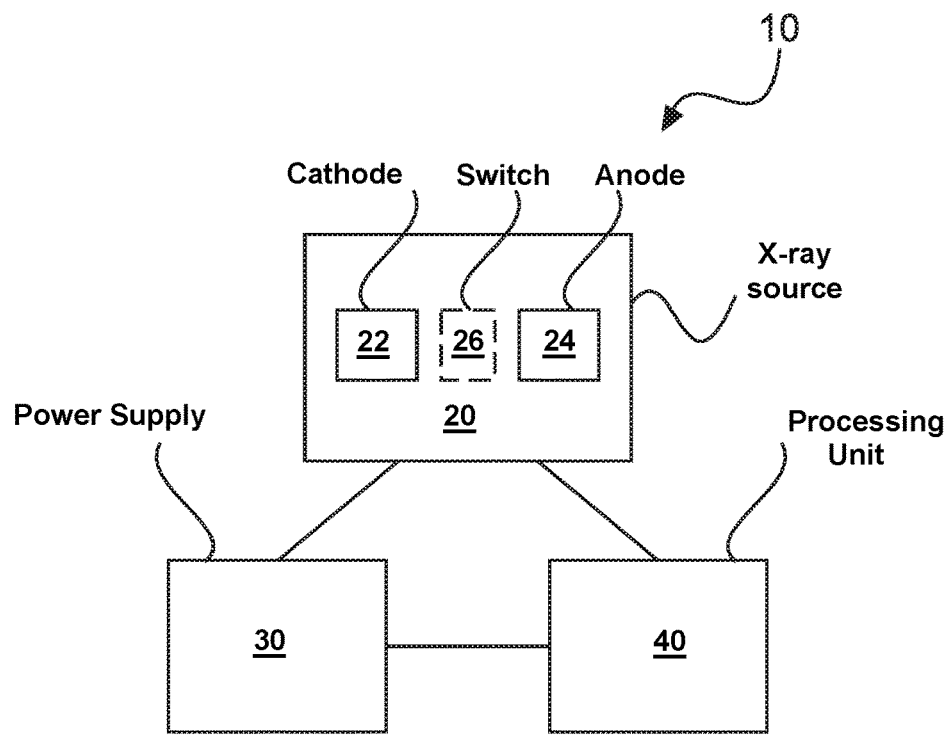
FIG. 1 shows a schematic set up of an example of an apparatus for generating X-rays.

FIG. 1 shows an example of an apparatus 10 for generating X-rays. The apparatus 10 comprises an X-ray source 20, a power supply 30, and a processing unit 40. The power supply 30 is configured to produce a voltage. The X-ray source 20 comprises a cathode 22 and an anode 24. The cathode 22 is positioned relative to the anode 24. The cathode 22 and anode 24 are operable such that electrons emitted from the cathode 22 interact with the anode 24 with energies corresponding to the voltage. The electrons interact with the anode 24 to generate X-rays. The processing unit 40 is configured to control the X-ray source 20, such that a plurality of first X-ray pulses is generated each having a first X-ray flux. The first X-ray pulses are temporally separated from each other. The processing unit 40 is also configured to control the X-ray source 20, such that at least one second X-ray pulse is generated having a second X-ray flux that is substantially less than the first X-ray flux. The processing unit 40 is configured such that the at least one second X-ray pulse is generated temporally between two consecutive pulses of the first X-ray pulses.

In an example, the processing unit is configured to control the X-ray source by controlling the power supply. In an example, the voltage of the power supply is controlled. In other words, the power supply voltage can switch high and low periodically, for example over different durations. In an example, the current supplied by the power supply is controlled. In other words, for example at a fixed voltage, the cathode current is switched on and off, or varied, periodically. For example, for fixed pulse duration the current can be at one level for the high flux pulse and at a lower level for the low flux pulse, and in another example the current can be at a certain level for a set time for a high flux pulse and at the same level, but for a shorter duration, for the low flux pulse. In an example, both the voltage and current of the power supply are controlled.

In an example, the at least one second X-ray pulse comprises two X-ray pulses. In an example, the at least one second X-ray pulse comprises three X-ray pulses. In an example, the at least one second X-ray pulse comprises four X-ray pulses. In an example, the at least one second X-ray pulse comprises more than four X-ray pulses, for example 5, 6, 7, or any number up to for example 20.

In an example, each of the at least one second X-ray pulses are substantially the same, with substantially the same pulse duration and substantially the same flux.

In an example, each of the first X-ray pulses has the same pulse duration.

In an example, the first X-ray pulses are temporally separated from each other by approximately 500 μs. In an example, the first X-ray pulses are temporally separated from each other by approximately 100 μs. In an example, the first X-ray pulses are temporally separated from each other by approximately 200 μs. In an example, the first X-ray pulses are temporally separated from each other by approximately 300 μs. In an example, the first X-ray pulses are temporally separated from each other by approximately 400 μs. In an example, the first X-ray pulses are temporally separated from each other by approximately 600 μs. In an example, the first X-ray pulses are temporally separated from each other by approximately 1000 μs, or by a duration between any of 100-1000 μs.

In an example, the processing unit is configured such that a series of X-ray pulses are generated, each of the series being substantially the same as the at least one second X-ray pulse, and wherein one of the series is generated temporally between all consecutive pulses of the first X-ray pulses. In other words, the apparatus can operate in a repeating manner, with one or more low flux pulses being generated between each pair of high flux pulses, where a repeating cycle can be 100-1000 μs.

According to an example, the processing unit 40 is configured to control a pulse duration of the plurality of first X-ray pulses and configured to control a pulse duration of the at least one second X-ray pulse.

In an example, a pulse of the plurality of first X-ray pulses has a duration of 100 μs. In an example, a pulse of the plurality of first X-ray pulses has a duration of 20 μs. In an example, a pulse of the plurality of first X-ray pulses has a duration of 40 μs. In an example, a pulse of the plurality of first X-ray pulses has a duration of 60 μs. In an example, a pulse of the plurality of first X-ray pulses has a duration of 80 μs. In an example, a pulse of the plurality of first X-ray pulses has a duration of 150 μs. In an example, a pulse of the plurality of first X-ray pulses has a duration of 200 μs. In an example, a pulse of the plurality of first X-ray pulses has a duration of 400 μs.

In an example, a pulse of the at least one second X-ray pulse has a duration of 1 μs. In an example, a pulse of the at least one second X-ray pulse has a duration less than 1 μs. In an example, a pulse of the at least one second X-ray pulse has a duration of 2 μs. In an example, a pulse of the at least one second X-ray pulse has a duration of 5 μs. In an example, a pulse of the at least one second X-ray pulse has a duration of 10 μs. In an example, a pulse of the at least one second X-ray pulse has a duration of 20 μs. In an example, a pulse of the at least one second X-ray pulse has a duration of 50 μs. In an example, a pulse of the at least one second X-ray pulse has a duration of 100 μs.

According to an example, an energy spectrum of the X-rays in the plurality of first X-ray pulses is substantially the same as an energy spectrum of the X-rays in the at least one second X-ray pulse. The ratio of the first X-ray flux to the second X-ray flux is substantially equal to the ratio of the pulse duration of each pulse of the plurality of first X-ray pulses to the pulse duration of the at least one second X-ray pulse.

According to an example, the X-ray source 20 comprises a switch 26 configured to inhibit the interaction of electrons between the cathode 22 and the anode 24. The processing unit 40 is configured to control the X-ray source by controlling the switch.

In other words, a switch that could be coupled to the power supply or coupled to a separate power supply, is controlled by the processing unit to periodically allow electrons emitted from the cathode to interact with the anode to produce pulses of different durations.

In an example, the switch comprises a grid positioned between the cathode and anode and wherein when the grid is held at a particular potential electrons can be emitted by the cathode and interact with the anode, and when the potential of the grid is changed there is no such interaction. In other words, grid switching of the X-ray source (such as an X-ray tube) is used with a rapid rise and fall time (about 1 μs or less than 1 μs) to provide X-ray beam modulation, enabling the X-ray flux to be controlled on a projection to projection basis.

According to an example, the switch 26 has a rise time of approximately 1 μs.

Figure 2:
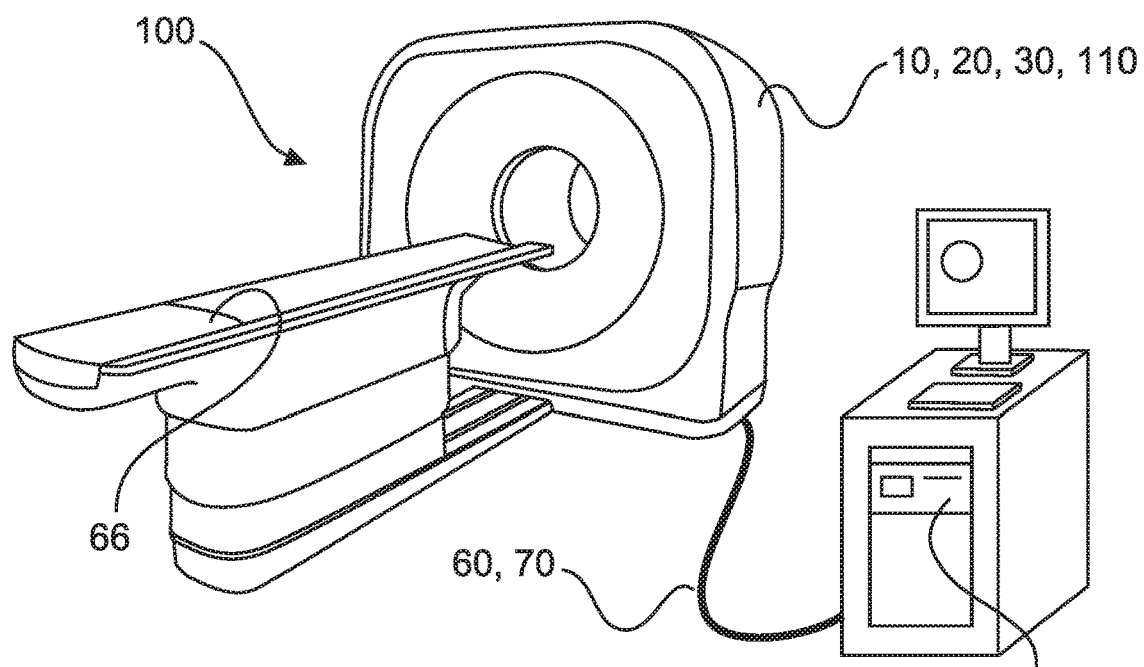
FIG. 2 shows a schematic set up of an example of a system for imaging an object.

FIG. 2 shows an example of a system 100 for imaging an object. The system 100 comprises an apparatus 10 for generating X-rays as described above with respect to any one or any combination of the examples of the apparatus shown in FIG. 1, and an X-ray detector 110. The X-ray detector 110, power supply 30, and X-ray source 20 are housed in the main housing, that in this example has a hole for accommodating a table 66 that can slide into the hole. Other geometries do not require a through hole or a table, and as such these features can be considered to be optional. A particular geometry of system is shown in FIG. 2, which is a CT scanner, however other system geometries are possible, with a different geometry of CT scanner (a C-arm scanner) shown in FIG. 11. The X-ray source 20 is configured to be positioned relative to the X-ray detector 110 such that at least a part of the region between them is an examination region for accommodating an object. The X-ray detector 110 is configured to acquire first data when a first one of the plurality of first X-ray pulses is generated, wherein the first data comprises spectral data. The X-ray detector 110 is also configured to acquire second data when the at least one second X-ray pulse is generated. The X-ray detector 110 is configured to acquire third data when a second one of the plurality of first X-ray pulses is generated, wherein the third data comprises spectral data. The processing unit 40 is configured to generate spectrally resolved image data comprising the first data and the third data. The processing unit 40 is also configured to generate spectrally integrated image data comprising the first data, the second data and the third data. Communication cable 60 leads from the X-ray detector 110 to the processing unit 40, and communication and cable 70 leads from the processing unit 40 to the power supply 30, X-ray source 20 and X-ray detector 110. These are shown as shown as a single cable, but can be separate cables. In an example, the power supply 30 can be housed with the processing unit 40. In such a case a communication cable 60 leads from the X-ray detector 110 to the processing unit 40, and combined communication and power cable 70 leads from the power supply 30 and processing unit 40 to the X-ray source 20 and X-ray detector 110.

In an example, the system is used for obtaining angular data of the object, with the X-ray source and detector rotating about the object acquiring data at different angular positions. Thus the system is useable to acquire data at numerous angular positions to form a "single scan", as would be recognized by the skilled person. With such a single scan, the system is therefore useable to obtain: 1) a high resolution (non spectral) image; 2) a spectral image with high signal to noise, with either reduced spatial resolution or limited field-of-view.

In an example, the first data is acquired at a first angular position with respect to an axis of the system, the second data is acquired at a second angular position with respect to the axis of the system, and the third data is acquired at a third angular position with respect to the axis of the system.

In an example, the processing unit is configured to use the spectrally resolved image data to perform a beam hardening correction on the spectrally integrated image data.

In an example, the processing unit is configured to use the spectrally integrated image data to perform a resolution correction on the spectrally resolved image data.

In this way, within such a hybrid system the non-spectral data can be used to improve or augment the spectral data, and/or the spectral data can be used to improve or augment the non-spectral data.

In this manner, the total noise (quantum and electronic noise) can be reduced per detector readout, leading to a significantly improvement in noise induced bias in addition to an improvement in the signal to noise.

According to an example, the processing unit 40 is configured to determine at least one measure of noise in the second data and wherein the second data comprises spectral data. On the basis of the at least one measure of noise the processing unit 40 is configured to generate spectrally resolved image data from the first data, the second data and the third data.

It is to be noted that the optional use of projection low flux data for the spectral image based on the noise in individual detection values may lead to irregular projection samples within a projection (pixel to pixel basis) and in the angular domain. This requires reconstruction techniques able to deal with irregular sampled data. However, so-called iterative reconstruction methods are able to deal with this and can benefit from the additional data relative to the exclusive use of high flux data.

According to an example, the X-ray detector 110 is configured to acquire energy dependent data at a first X-ray energy and acquire energy dependent data at a second X-ray energy.

In an example, the X-ray detector is a dual layer detector. This provides for a simple means for acquiring spectral energy data useable to provide spectral imaging.

In an example, the detector comprises two scintillators each having a different spectral sensitivity.

According to an example, the first data comprises first energy dependent data at the first X-ray energy and first energy dependent data at the second X-ray energy, and the third data comprises third energy dependent data at the first X-ray energy and third energy dependent data at the second X-ray energy.

According to an example, the second data comprises spectral data and the second data comprises second energy dependent data at the first X-ray energy and second energy dependent data at the second X-ray energy. The processing unit 40 is configured to generate a first combined data from the first energy dependent data at the first X-ray energy and the first energy dependent data at the second X-ray energy, and generate a second combined data from the second energy dependent data at the first X-ray energy and the second energy dependent data at the second X-ray energy, and generate a third combined data from the third energy dependent data at the first X-ray energy and the third energy dependent data at the second X-ray energy. The spectrally integrated image data is generated from the first combined image, the second combined image and the third combined image.

In an example, the processing unit is configured to determine a measure of noise in the second energy dependent data at the first X-ray energy and determine a measure of noise in the second energy dependent data at the second X-ray energy; and on the basis of the measures of noise, the processing unit is configured to generate spectrally resolved image data from the first energy dependent data at the first X-ray energy, the first energy dependent data at the second X-ray energy, the second energy dependent data at the first X-ray energy and/or the second energy dependent data at the second X-ray energy, the third energy dependent data at the first X-ray energy, and the third energy dependent data at the second X-ray energy.

In other words, all of the data can be used to provide spectral image data, even when for one shot only data for one half of the detector is used for that shot.

In an example, the system comprises an output unit configured to output data representative of the spectrally resolved image data. In an example, the system comprises an output unit configured to output data representative of the spectrally resolved image data and the spectrally integrated imaged data.

In an example, the system comprises a C-arm CT system. In other examples, different types of image acquisition configurations are used.

Figure 3:
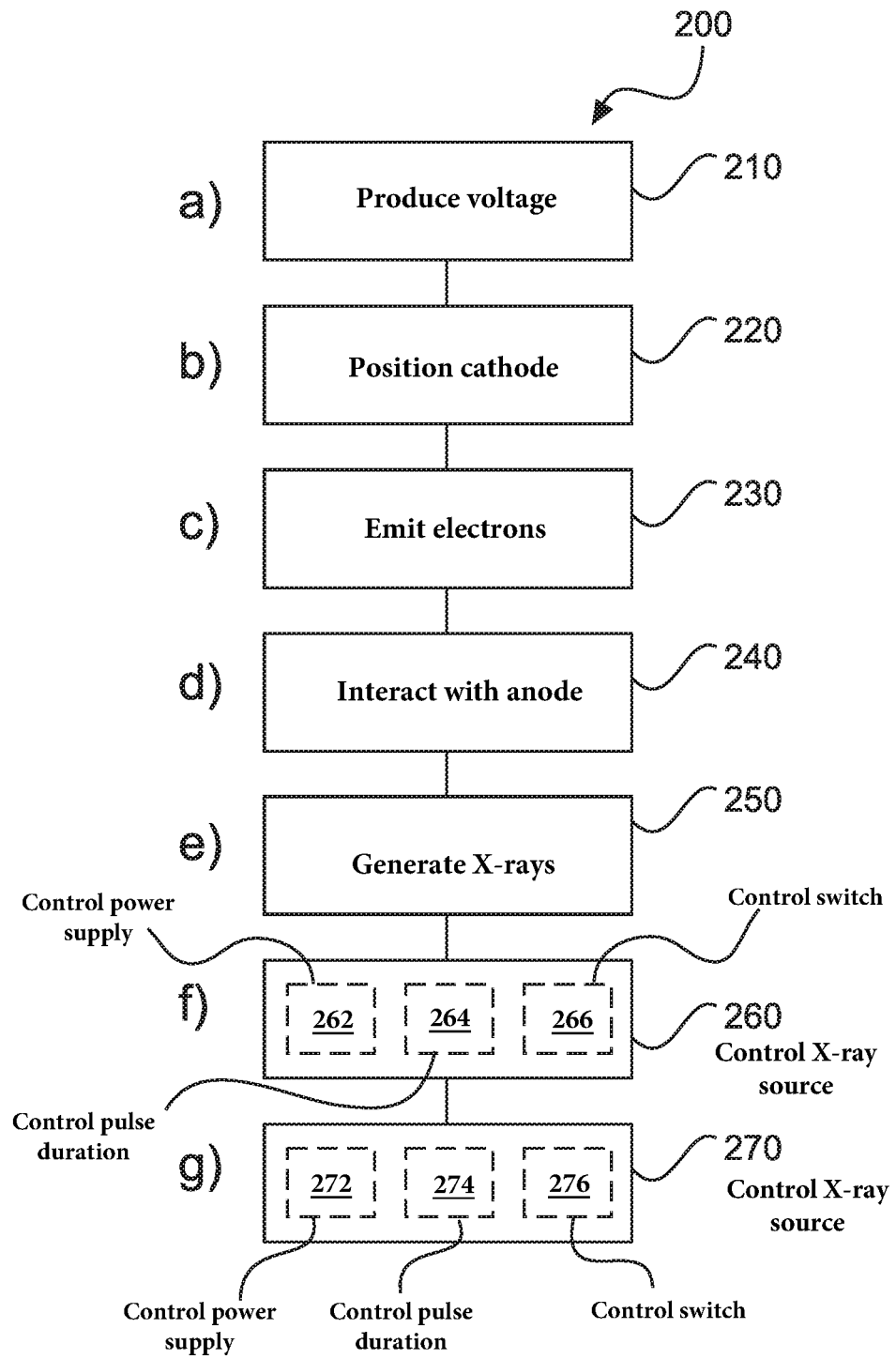
FIG. 3 shows a method for generating X-rays.

FIG. 3 shows a method 200 for generating X-rays in its basic steps. The method 200 comprises:

in a producing step 210, also referred to as step a), a power supply 30 produces a voltage;

in a positioning step 220, also referred to as step b), a cathode 22 of an X-ray source 20 is positioned relative to an anode 24 of the X-ray source;

in an emitting step 230, also referred to as step c), electrons are emitted from the cathode;

in an interacting step 240, also referred to as step d), electrons emitted from the cathode interact with the anode with energies corresponding to the voltage;

in a generating step 250, also referred to as step e), X-rays are generated from the anode, wherein the electrons interact with the anode to generate the X-rays;

in a controlling step 260, also referred to as step f), the X-ray source is controlled, such that a plurality of first X-ray pulses is generated each having a first X-ray flux, wherein the first X-ray pulses are temporally separated from each other;

in a controlling step 270, also referred to as step g), the X-ray source is controlled, such that a least one second X-ray pulse is generated having a second X-ray flux that is substantially less than the first X-ray flux, wherein the at least one second X-ray pulse is generated temporally between consecutive pulses of the first X-ray pulses.

In the method above, step b) is referred to as a positioning step, but this does not mean that there needs to be any movement between the cathode and anode of the X-ray source, and can mean that the anode and cathode are poisoned relative to one another, which could be in a fixed geometry.

In an example, step f) comprises controlling 262 the power supply 30.

In an example, step f) comprises controlling 264 a pulse duration of each of the plurality of first X-ray pulses.

In an example, step g) comprises controlling 272 the power supply 30.

In an example, step g) comprises controlling 274 a pulse duration of the at least one second X-ray pulse.

In an example, the X-ray source 20 comprises a switch 26 configured to inhibit the interaction of electrons between the cathode and the anode; and wherein step f) comprises controlling 266 the switch.

In an example, the X-ray source 20 comprises a switch 26 configured to inhibit the interaction of electrons between the cathode and the anode; and wherein step g) comprises controlling 276 the switch.

Figure 4:
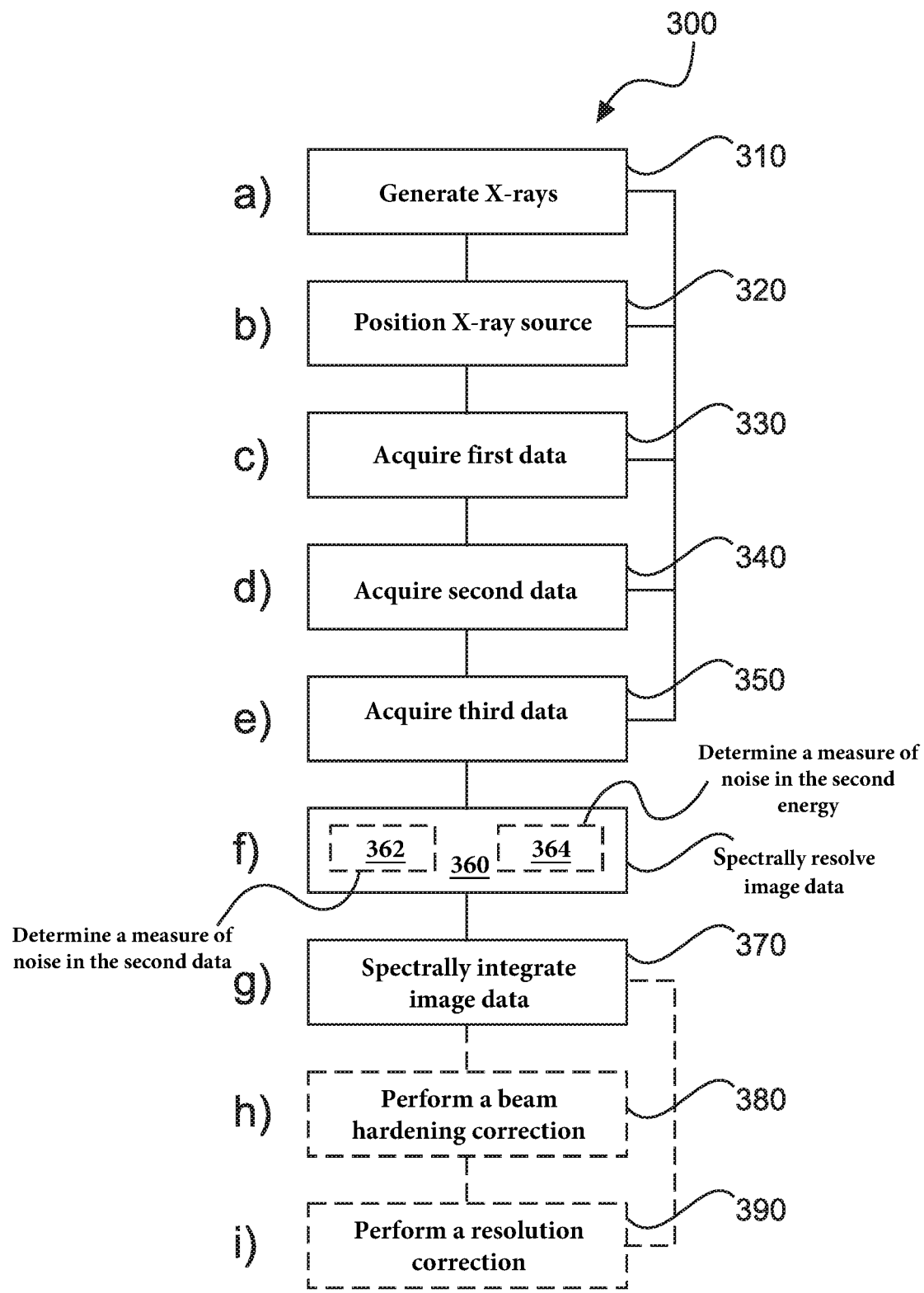
FIG. 4 shows a method for imaging an object.

FIG. 4 shows a method 300 for imaging an object in its basic step. The method 300 comprises:

in a generating step 310, also referred to as step a), X-rays are generated from an X-ray source 20 as described above with respect to the method shown in FIG. 3;

in a positioning step 320, also referred to a step b), the X-ray source is positioned relative to an X-ray detector 110 such that at least a part of the region between them is an examination region for accommodating an object;

in an acquiring step 330, also referred to as step c), first data are acquired when a first one of the plurality of first X-ray pulses is generated, wherein the first data comprises spectral data;

in an acquiring step 340, also referred to as step d), second data are acquired when the at least one second X-ray pulse is generated;

in an acquiring step 350, also referred to as step e), third data are acquired when a second one of the plurality of first X-ray pulses is generated, wherein the third data comprises spectral data;

in a generating step 360, also referred to as step f), spectrally resolved image data are generated from the first data and the third data; and in a generating step 370, also referred to as step g), spectrally integrated image data are generated from the first data, the second data and the third data.

In the method above, step b) is referred to as a positioning step, but this does not mean that there needs to be any movement between the X-ray source and anode of the detector, and can mean that the X-ray source and detector are poisoned relative to one another, which could be in a fixed geometry, albeit both rotating around an axis but at a constant separation. However, the X-ray source and detector can be moved closer together or moved away from one another, as required.

In an example of the method 300 for imaging an object, step a) is the method 200 for generating X-rays in its basic steps, but can be method 200 including any combination of the optional method steps described in association with FIG. 3.

In an example, the method comprises step h), using 380 the spectrally resolved image data to perform a beam hardening correction on the spectrally integrated image data.

In an example, the method comprises step i), using 390 the spectrally integrated image data to perform a resolution correction on the spectrally resolved image data.

In an example, the second data comprises spectral data and step f) comprises determining 362 at least one measure of noise in the second data; and on the basis of the at least one measure of noise the spectrally resolved image data is generated from the first data, the second data and the spectral data.

In an example, the X-ray detector is configured to acquire data at a first X-ray energy and acquire data at a second X-ray energy.

In an example, the first data comprises first energy dependent data at the first X-ray energy and first energy dependent data at the second X-ray energy, and the third data comprises third energy dependent data at the first X-ray energy and third energy dependent data at the second X-ray energy.

In an example, the second data comprises spectral data and the second data comprises second energy dependent data at the first X-ray energy and second energy dependent data at the second X-ray energy. The method then comprises generating a first combined data from the first energy dependent data at the first X-ray energy and the first energy dependent data at the second X-ray energy, and generating a second combined data from the second energy dependent data at the first X-ray energy and the second energy dependent data at the second X-ray energy, and generating a third combined data from the third energy dependent data at the first X-ray energy and the third energy dependent data at the second X-ray energy. Step g) then comprises generating spectrally integrated image data from the first combined image, the second combined image and the third combined image.

In an example, step f) comprises determining 364 a measure of noise in the second energy dependent data at the first X-ray energy and determining a measure of noise in the second energy dependent data at the second X-ray energy. On the basis of the measures of noise, the spectrally resolved image data is generated from the first energy dependent data at the first X-ray energy, the first energy dependent data at the second X-ray energy, the second energy dependent data at the first X-ray energy and/or the second energy dependent data at the second X-ray energy, the third energy dependent data at the first X-ray energy, and the third energy dependent data at the second X-ray energy.

Examples of the apparatus and method for generating X-rays and the system and method for imaging an object will now be described in more detail in conjunction with FIGS. 5-10.

CT Detection Noise Reduction by Sparse Sampling

Scintillator based CT detectors suffer from electronic noise. Although the noise level is low, it can become dominant if the incident X-ray flux becomes very low. Improvements in CT imaging, such as the use of advanced iterative reconstruction, allow for ultra-low dose scanning and detection noise becomes of increasing importance and can become a limitation. To address this, sparse acquisition is carried out using X-ray tube grid switching (GS), where the grid switched X-ray tube allows for ultra-fast (rise and fall time about 1 µs) X-ray beam modulation. Tube grid switching is a well-known technique to control the electron beam between the cathode and the anode of a conventional X-ray tube. The technique is used in commercial X-ray fluoroscopy machines. The same technique (with fast switching times) is here used to modulate the X-ray flux. The basic principles of this tube technology is discussed in R. Behling, Modern Diagnostic X-ray Sources, CRC Press. Therefore, it becomes possible to control the X-ray flux on a project-to-projection basis. It becomes possible to rapidly control the mean flux within a single projection acquisition (~100 µs or longer) using X-ray pulse width modulation. The X-ray flux can also be modulated for constant durations by varying the current and/or voltage for different pulses.

Using GS angular sub-sampling is performed. As the system shown in FIG. 2 rotates about the object, such as a human, at one level spectral data can be obtained by sampling only every other view and modulating the X-ray beam accordingly using GS. If the X-ray tube flux is doubled during the sparse acquisitions, the same total X-ray dose for the entire acquisition is obtained with respect to having sampled at every view with a non-doubled flux. However the X-ray flux on the detector per used projection has been doubled and thus the electronic noise issue explained above is reduced.

Sparse Angular Sampling for Dual Layer Spectral CT

Figure 10:
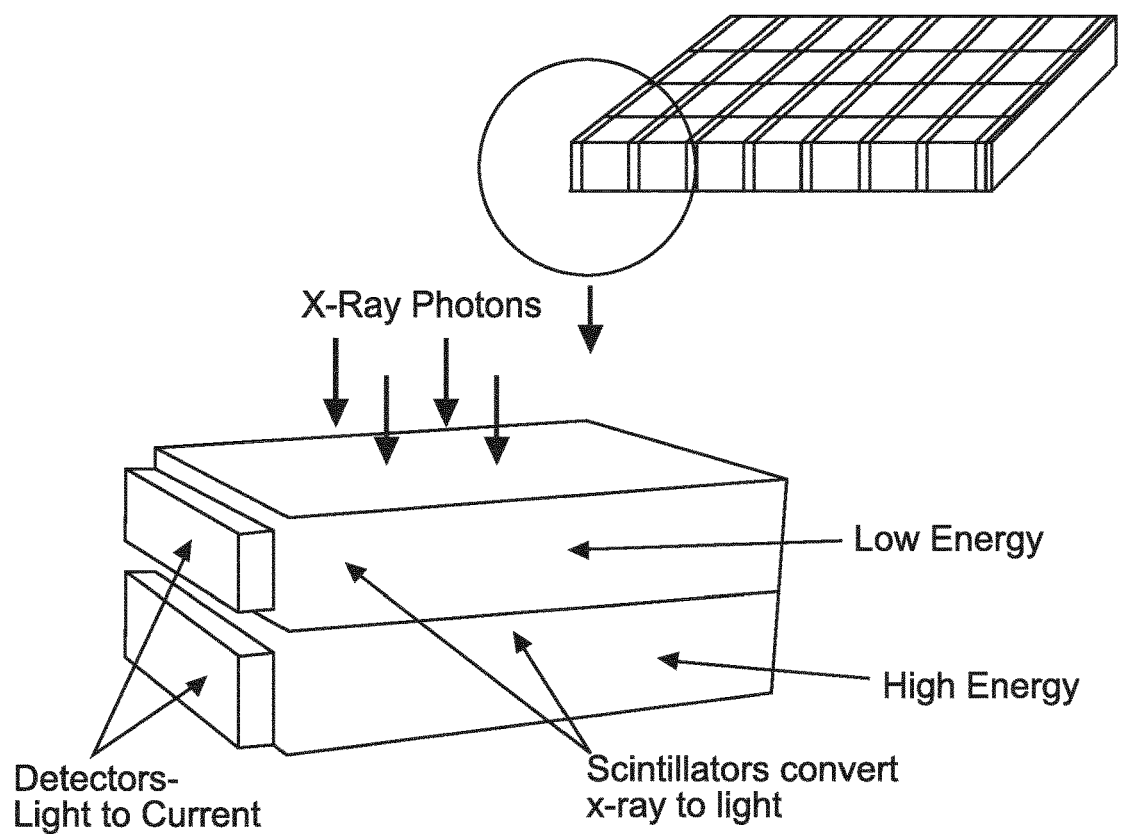
FIG. 10 shows an example of a dual energy detector.

In Dual Layer detection (DL) a stack of two scintillators, as shown in FIG. 10, is used to obtain spectral information by different effective spectral sensitivities of the layers. X-rays are absorbed in the layers with photons being generated that are detected by a side looking photodiode. The top layer of the scintillator absorbs low energy X-rays with each top level scintillators pixel having an associated photodiode pixel, and similarly the bottom layer of the scintillator absorbs high energy X-ray, which are detected by a photodiode. The electronics per channel is identical to a conventional detector and hence noise suffers from electronic noise. However the problem is exacerbated when spectral data are being acquired by dual layer detection. Even under ideal conditions the total incident flux is equally shared by the two layers, the flux seen by one layer is then only 50% compared to that for conventional detection. Under realistic conditions the flux is not balanced and often one of the layers may get only a low flux, with the other layer getting a higher flux. Therefore, there is a reduction in signal to noise.

In addition to the detection noise problem, spectral imaging suffers from an effect called noise induced bias. To obtain spectral information (such as VNC or Iodine maps) from DL detection the data from the two channels has to undergo a (non-linear) material separation process. The process tends to generate a bias for noisy input data. The bias has a significant negative impact on the quality of the images and becomes a problem for quantification. However, sparse sampling can significantly improve the bias problem and is an additional benefit of GS based sparse sampling, due to the reduction of the total noise (quantum and electronic noise) per detector readout.

Figure 5:
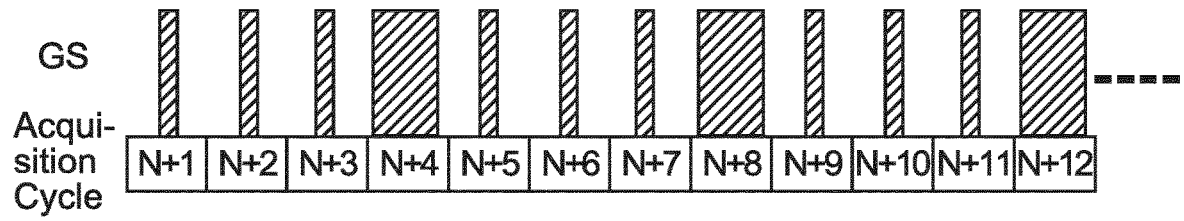
FIG. 5 shows an example of a series of flux pulses generated by an apparatus for generating X-rays.
Figure 6:
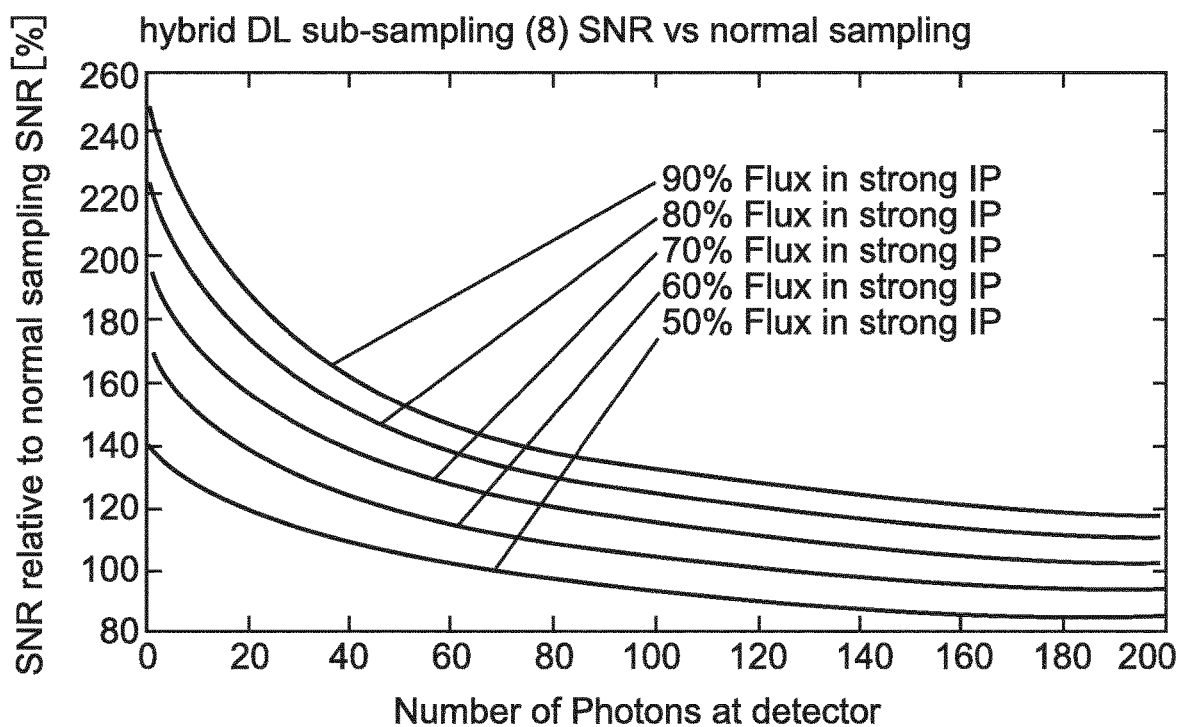
FIG. 6 shows an example of signal to noise ratio for hybrid sparse sampling with respect to nominal sampling.

FIG. 5 shows an example of an x-ray tube modulation pattern, which continues to repeat in this manner. In a series of acquisition cycles with a relatively low effective dose (or flux), one cycle has a much higher dose (flux), with the low flux cycles being temporally interspersed between consecutive high flux pulses. This modulation pattern enables a hybrid sparse sampling approach, combining the high image quality of moderate sparse or even full angular sampling (no sparse) for conventional (non-spectral) imaging with sparse sampling for spectral imaging. In the hybrid approach, the reconstruction of the conventional and spectral data is done differently. The conventional image reconstruction uses all the projections, with each of the acquisition cycles as shown in FIG. 5 being used for projection, and therefore will not suffer from angular sub-sampling, or only moderately suffer. However, spectral reconstruction uses only those projections corresponding to high flux acquisitions, shown in FIG. 5 at positions N+4, N+8, N+12.

SNR Gain for Hybrid Sparse Sampling

The following provides details of how hybrid sparse sampling can lead to an improvement in signal-to-noise. Consider a sequence of "s" samples with a nominal flux of "n" photons per sample. If these samples are combined, a signal-to-noise ratio of $$SNR_{Nominal} = \frac{ns}{\sqrt{ns + se}}$$

results, with "e" being the photon equivalent variance of the electronic noise. With hybrid sparse sampling, if one sample with a higher flux of ñ=fsn is used with "f" being the fraction of the total flux in this single sample, then a signal-to-noise ratio of $$SNR_{Hybrid} = \frac{\tilde{n}}{\sqrt{\tilde{n} + e}}$$

results. In other words "f" is the fraction of the flux detected in one half of the dual layer detector that is being considered, but the overall flux has been increased in this one pulse to match that over all the previously considered s pulses. A comparison of the SNR is plotted in FIG. 6. It clearly shows that even though only a fraction of photons "f" is being detected, the loss in SNR is outweighed by the fact that there is a smaller contribution from electronic noise.

In FIG. 5, all the pulses including those with a high flux are used to provide high resolution conventional imaging, with the signals from the 2 halves of the dual layer detector added to former spectrally integrated signal. However, the signal levels are monitored and if the detected signal for a low flux acquisition is high enough, for example the object at this angular position is not very absorbing, then this low flux acquisition in addition to being used in the conventional imaging can also be used for spectral imaging along with the acquisitions corresponding to the high flux cases. This is because, spectral data from the 2 halves of the detector has been acquired, which as described above is added together for the conventional (non-spectral) imaging but is used as the 2 separate signals as part of the spectral imaging. In this way, there is no loss of SNR in high flux sequences.

Figure 7:
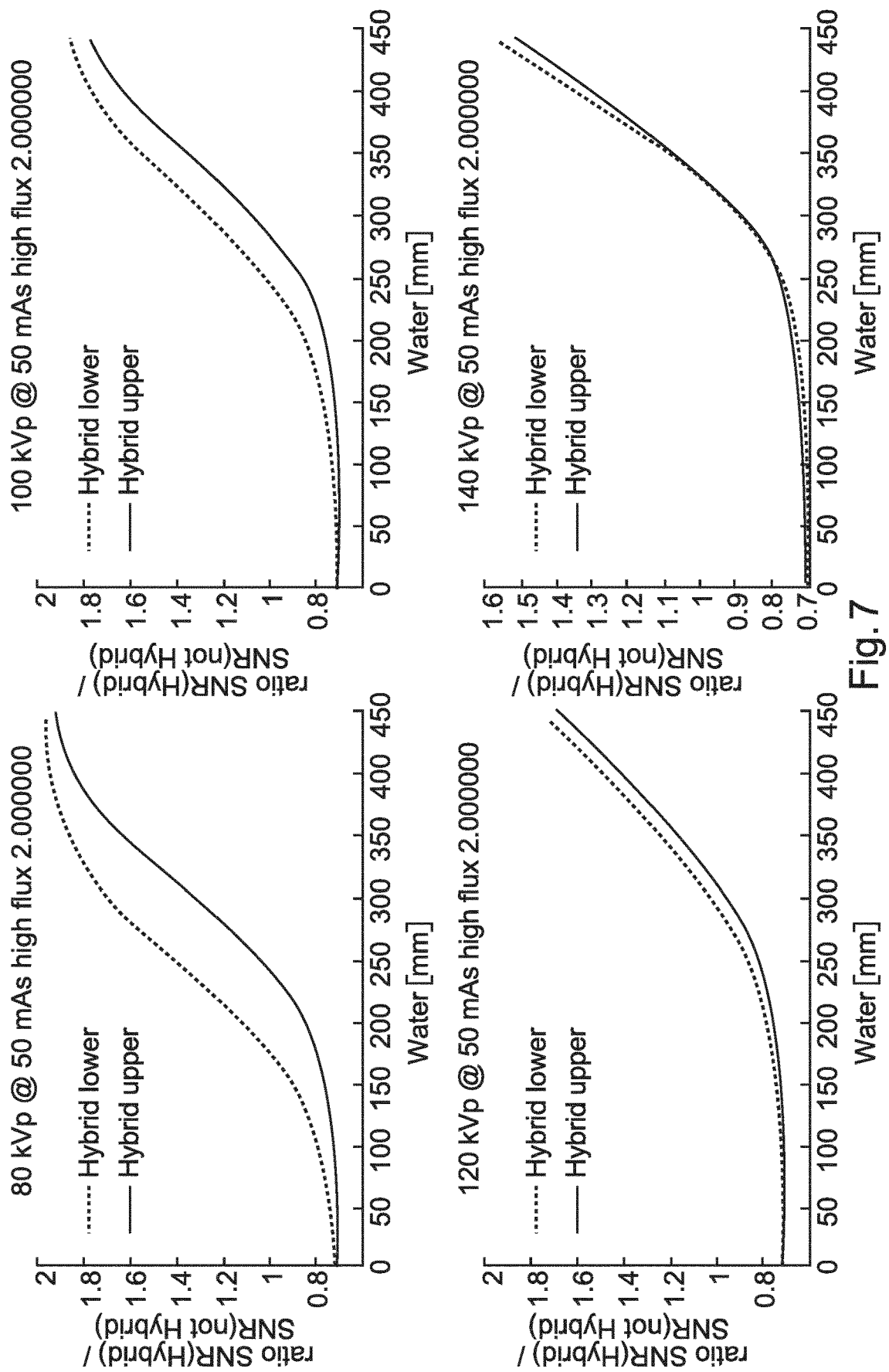
FIG. 7 shows an example of signal to noise ratio for hybrid sampling with respect to nominal sampling at various energies and absorptions.

FIG. 7 shows the results of a numerical study for various spectra (related to 80, 100, 120 and 140 kVp tube voltage) and absorptions (0 to 450 mm water). In these figures "f" is equal to 0.5, indicating that 50% of the total flux of "s" consecutive pulses is in the high flux pulse, and "s" is 4 indicating that three low flux pulses follow every high flux pulse. FIG. 7 indicates the expected signal to noise gain for the hybrid spectral data, determined from the dual layer detector for various energies and absorptions. The varying water absorption length (0 to 450 mm) generate different spectra for the detection unit and therefore change the flux sharing between the two layers of the detector. With more water absorption, the X-ray beam gets harder and the second detection layer gets increased flux relative two the first layer.

Noise Induced Bias for Hybrid Sparse Sampling

Noise induced bias, resulting from the processing of noisy spectral data, is mentioned above and discussed in more detail here. Bias in the projection data and in the resulting images forms a problem for quantitative imagery, since the (mean) attenuation values depend on the noise in the acquired data. Although the bias is a deterministic function of the expected value and noise in the data, it is difficult to estimate and correct for, since the estimation would suffer from the fact that it must be derived from a noisy data sample without the knowledge of the expected value itself. Therefore, noise induced bias can be mitigated by improving the signal to noise, with the following providing more details.

For simplicity, it is assumed that a logarithm of the acquired data can be determined as part of image reconstruction, in order to model a simple nonlinear processing function of the data. Typically, the logarithm is used to convert the measured detector signal to linear absorption line integrals for the reconstruction, and therefore this simple measure provides an indication of the required processing. Even if this function is not explicitly performed, the transformation has conceptually to be applied to the data and may be hidden somewhere, and therefore serves as a means to examine data fidelity.

Figure 8:
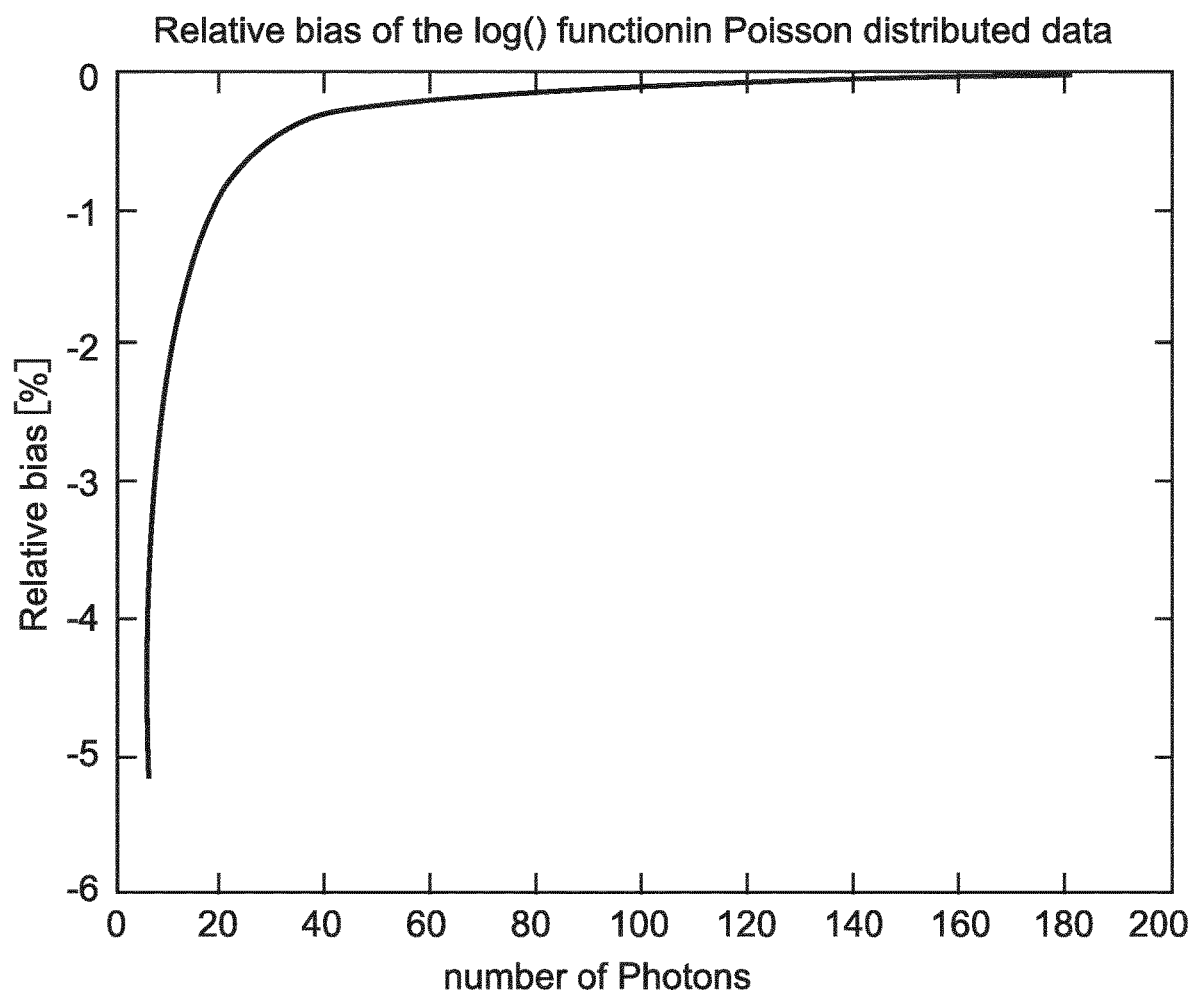
FIG. 8 shows exemplar data representative of noise induced bias in spectral data.

If there are "n" photons, arriving at the detector with Poisson arrival distribution, the expected bias from the logarithm is b=E(log X(n))−log n, with X(n) being a Poisson distributed random variable with mean "n". FIG. 8 shows a numerical evaluation of the relative bias $$\tilde{b} = \frac{E(\log X(n)) - \log n}{\log n}.$$

Figure 9:
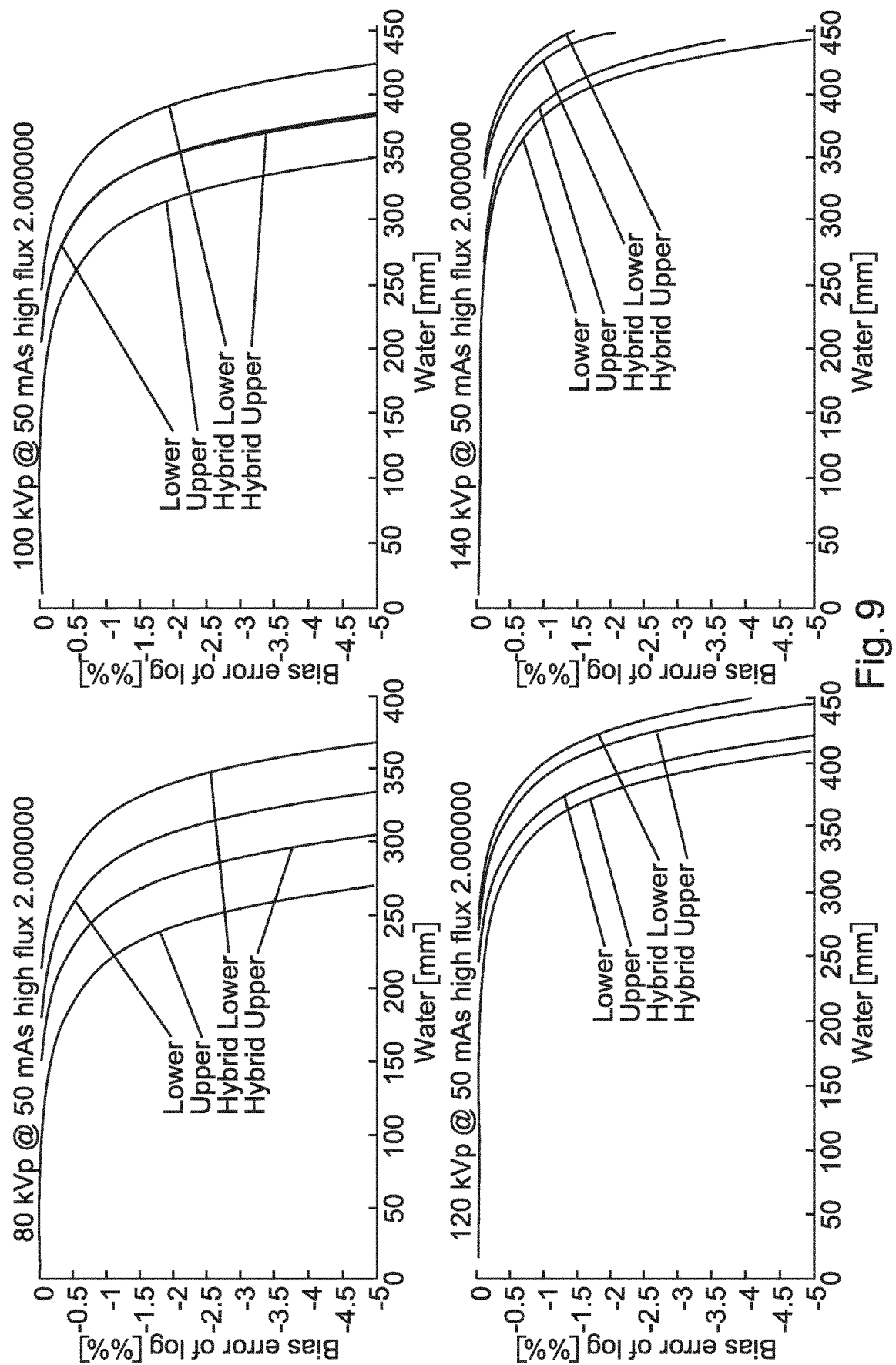
FIG. 9 shows an example of noise induced bias at various energies and absorptions.

Because of numerical instabilities, the simulation has been restricted to cases of 6 or more photons arriving at the detector. This indicates the issues surrounding low signals, which lead to noisy signals. A dual layer system simulation of the impact of hybrid sparse sampling is shown in FIG. 9, which shows the noise induced bias for various energies and absorptions for both sparse and non-sparse sampling, highlighting that sparse sampling mitigate noise induced bias. For the simulation resulting in the data shown in FIG. 9, again "f"=0.5, and "s"=4.

FIG. 10 shows a dual layer detector array, with one pixel of that array shown in an expanded view. A detector pixel is made from two scintillators stacked one on top of the other, with X-rays being incident from the top. Low energy X-rays are absorbed in the top scintillators, with absorption leading to the emission of longer wavelength radiation that is detected by a photodiode that is positioned on the lateral side of that scintillators. The bottom scintillator absorbs high energy X-rays and again re-emitted longer wavelength radiation is detected by a second photodiode associated with that scintillator.

Figure 11:
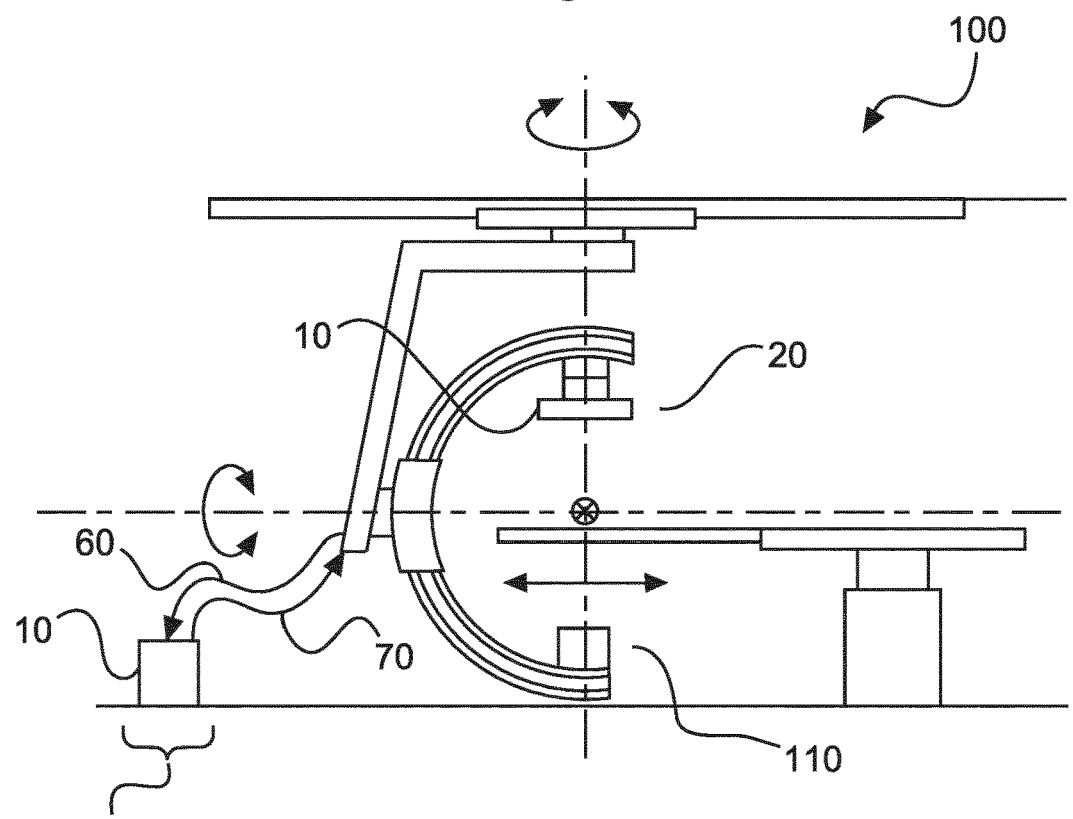
FIG. 11 shows a schematic set up of an example of a system for imaging an object.

FIG. 11 shows another example of a system for imaging an object to that shown in FIG. 2, where this geometry is a C-arm set-up.

Beam Hardening Correction

In the present hybrid system, the sparse spectral data can be used to correct for beam hardening in the high resolution non-spectral data. It is to be noted that the term beam hardening refers to the physical effect that the spectrum of the X-ray beam gets relatively more high energy photons (becomes harder) when passing through the object. If the image acquisition cannot resolve for this none linear energy absorption, the estimation of the linear attenuation coefficient from the detector readings is not unique anymore. A usual solution to the problem takes the theoretical spectral response of the imaging device and assumes water (or soft tissue) to be responsible for the attenuation. With these assumptions, a so-called water-beam-hardening-correction can be performed. This works sufficiently if water, or a water like absorber such as soft tissue, dominates the absorption. However, if other elements such as calcium (bones) or iodine (contrast agent) with larger atomic numbers become relevant, this first order correction fails and generates so-called beam hardening artifacts. More advanced methods do a first reconstruction and segment the bone in the resulting image. With the identified bone, an improved correction can be applied to the projection data assuming the spectral attenuation of this bone. Therefore, the contribution of bone attenuation is estimated by a forward projection of the bone image. In a second reconstruction, the corrected projections data are used to generate the corrected images. These types of correction methods are called 2nd pass beam hardening correction. It is to be noted that the artefacts and the related corrections have typically only low spatial frequency components.

For hybrid sparse sampling according to the present apparatus, system and methods, the low spatial frequency spectral data can be used to perform a beam hardening correction for the conventional image. Two methods can be used to implement this correction:

A spectral material decomposition (e.g. water, bone) is performed for the high flux readings. A correction factor is calculated and applied for the combined detector values. The correction factors for the low flux readings are interpolated from the geometrical neighbor data with high flux.

Effectively a so-called 2nd pass beam hardening is applied where the bone image is obtained from a spectral material decomposition and reconstruction yielding a bone image.

These basic principles of beam hardening correction can be applied to other materials with high atomic numbers such as iodine or metal (e.g. implants).

Correction of Spectral Images from Conventional Images

In the present hybrid system, the non-spectral data can be used to improve the sparse spectral data, where the higher spatial resolution and the reduced noise of the conventional image is used to improve the spectral images. First, it is briefly discussed why sparse sampling leads to limited spatial resolution and then it is discussed how the conventional non-spectral can be used to improve this.

CT data acquisition acquires discrete data samples. The reconstruction transfers these data to discrete images. The spatial sampling and signal frequencies of the data representation must fulfil some Nyquist conditions to avoid aliasing artefacts. The problem is discussed in K. Kak and M. Slaney "Principles of Computerized Tomographic Imaging", p. 177 ff, SIAM, in applied mathematics. For a required spatial resolution in the image domain, the sampling frequency of the acquisition must fulfil minimal requirements to avoid aliasing. If we the angular sampling frequency (angular sub-sampling) is reduced, which is done here for the high flux pulses being used to generate spectral data using sparse sampling, only generate limited spatial resolution can be generated in the image domain. Since the number of angular high flux projections is limited the projection data needs to be filtered accordingly, from which only limited spatial resolution can be generated compared to full angular sampling.

Regarding improving this situation using the non-spectral data, one powerful method, called structured propagation assumes that the structure properties in the images (non-spectral and spectral) are very similar (e.g. edges are at the same position). In combination with a noise model of the images an objective function can be formulated and numerically optimized to propagate the structure of the conventional (non-spectral) image into the spectral images. Such a methodology is described in WO2014128595 A1. In this way, the conventional high resolution image can be used to improve the resolution in the spectral image.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for generating X-rays, comprising:
a power supply configured to produce a voltage;
an X-ray source comprising a cathode and an anode, wherein the cathode is positioned relative to the anode, and the cathode and anode are operable such that electrons emitted from the cathode interact with the anode with energies corresponding to the voltage, and wherein the electrons interact with the anode to generate the X-rays; and
at least one processor configured to:
control the X-ray source such that a plurality of first X-ray pulses is generated, each having a first X-ray flux, wherein the first X-ray pulses are temporally separated from each other;
control the X-ray source such that at least one second X-ray pulse is generated having a second X-ray flux that is substantially less than the first X-ray flux; wherein the at least one second X-ray pulse is generated temporally between two consecutive pulses of the first X-ray pulses.

2. The apparatus according to claim 1, wherein the at least one processor is configured to control a pulse duration of the plurality of first X-ray pulses and control a pulse duration of the at least one second X-ray pulse.

3. The apparatus according to claim 2, wherein the ratio of the first X-ray flux to the second X-ray flux is substantially equal to the ratio of the pulse duration of each pulse of the plurality of first X-ray pulses to the pulse duration of the at least one second X-ray pulse.

4. The apparatus according to claim 1, wherein the X-ray source comprises a switch configured to inhibit the interaction of electrons between the cathode and the anode; and wherein the at least one processor is configured to control the X-ray source by controlling the switch.

5. The apparatus according to claim 4, wherein the switch has a rise time of approximately 1 μs.

6. A system for imaging an object, comprising:
a power supply configured to produce a voltage;
an X-ray source comprising a cathode and an anode, wherein the cathode is positioned relative to the anode, and the cathode and anode are operable such that electrons emitted from the cathode interact with the anode with energies corresponding to the voltage, and wherein the electrons interact with the anode to generate X-rays;
at least one processor configured to:
control the X-ray source such that a plurality of first X-ray pulses is generated, each having a first X-ray flux, wherein the first X-ray pulses are separated from each other;
control the X-ray source such that at least one second X-ray pulse is generated having a second X-ray flux that is substantially less than the first X-ray flux, wherein the at least one second X-ray pulse is generated temporally between two consecutive pulses of the first X-ray pulses; and
an X-ray detector configured to:
acquire first data when a first one of the plurality of first X-ray pulses is generated;
acquire second data when the at least one second X-ray pulse is generated;
acquire third data when a second one of the plurality of first X-ray pulses is generated, wherein the first data and the third data comprise spectral data;
wherein the at least one processor is further configured to:
generate spectrally resolved image data comprising the first data and the third data; and
generate spectrally integrated image data comprising the first data, the second data and the third data.

7. The system according to claim 6, wherein the at least one processor is configured to determine at least one measure of noise in the second data, and wherein the second data comprises spectral data; and based on the at least one measure of noise the at least one processor is configured to generate spectrally resolved image data from the first data, the second data and the third data.

8. The system according to claim 6, wherein; the X-ray detector is configured to acquire energy dependent data at a first X-ray energy and acquire energy dependent data at a second X-ray energy.

9. The system according to claim 8, wherein the first data comprises first energy dependent data at the first X-ray energy and first energy dependent data at the second X-ray energy, and the third data comprises third energy dependent data at the first X-ray energy and third energy dependent data at the second X-ray energy.

10. The system according to claim 9, wherein the second data comprises spectral data, and the second data comprises second energy dependent data at the first X-ray energy and second energy dependent data at the second X-ray energy; and wherein the at least one processor is configured to generate a first combined data from the first energy dependent data at the first X-ray energy and the first energy dependent data at the second X-ray energy, and generate a second combined data from the second energy dependent data at the first X-ray energy and the second energy dependent data at the second X-ray energy, and generate a third combined data from the third energy dependent data at the first X-ray energy and the third energy dependent data at the second X-ray energy; and wherein the spectrally integrated image data is generated from the first combined image, the second combined image and the third combined image.

11. A method for generating X-rays, comprising:
producing a voltage with a power supply;
positioning a cathode of an X-ray source relative to an anode of the X-ray source;
emitting electrons from the cathode;
interacting the electrons emitted from the cathode with the anode with energies corresponding to the voltage;
generating the X-rays from the anode, wherein the electrons interact with the anode to generate the X-rays;
controlling the X-ray source; such that a plurality of first X-ray pulses is generated, each having a first X-ray flux, wherein the first X-ray pulses are temporally separated from each other;
controlling the X-ray source; such that a least one second X-ray pulse is generated having a second X-ray flux that is substantially less than the first X-ray flux, wherein the at least one second X-ray pulse is generated temporally between consecutive pulses of the first X-ray pulses; and wherein an energy spectrum of the X-rays in the plurality of first X-ray pulses is substantially the same as an energy spectrum of the X-rays in the at least one second X-ray pulse.

12. A non-transitory computer-readable medium having one or more executable instructions stored thereon which, when executed by at least one processor, cause the at least one processor to perform the method of claim 11.

13. A method for imaging an object, comprising:
generating X-rays from an X-ray source;
producing with a power supply a voltage;
positioning a cathode of the X-ray source relative to an anode of the X-ray source;
emitting electrons from the cathode;
interacting the electrons emitted from the cathode with the anode with energies corresponding to the voltage;
generating the X-rays from the anode, wherein the electrons interact with the anode to generate the X-rays;
controlling the X-ray source; such that a plurality of first X-ray pulses is generated, each having a first X-ray flux, wherein the first X-ray pulses are temporally separated from each other;
controlling the X-ray source; such that a least one second X-ray pulse is generated having a second X-ray flux that is substantially less than the first X-ray flux, wherein the at least one second X-ray pulse is generated temporally between consecutive pulses of the first X-ray pulses;
positioning the X-ray source relative to an X-ray detector such that at least a part of the region therebetween is an examination region for accommodating an object;
acquiring first data when a first one of the plurality of first X-ray pulses is generated, wherein the first data comprises spectral data;
acquiring second data when the at least one second X-ray pulse is generated;
acquiring third data when a second one of the plurality of first X-ray pulses is generated, wherein the third data comprises spectral data;
generating spectrally resolved image data from the first data and the third data; and
generating spectrally integrated image data from the first data, the second data and the third data.

14. A non-transitory computer-readable medium having one or more executable instructions stored thereon which, when executed by at least one processor, cause the at least one processor to perform the method of claim 13.

\* \* \* \* \*